United States Patent [19]

Yoshida et al.

[11] Patent Number: 4,593,973
[45] Date of Patent: Jun. 10, 1986

[54] COMPOSITE OPTICAL FIBER AND IMAGING CATHETER AND METHOD FOR PRODUCING THE SAME

[75] Inventors: Kenichi Yoshida; Kimizo Ono; Koichi Tsuno, all of Osaka, Japan

[73] Assignee: Sumitomo Electric Industries, Ltd., Osaka, Japan

[21] Appl. No.: 507,643

[22] Filed: Jun. 27, 1983

[30] Foreign Application Priority Data

Jun. 26, 1982 [JP] Japan ................... 57-110151

[51] Int. Cl.[4] ..................... G02B 6/02; B29D 11/00
[52] U.S. Cl. .................... 350/96.29; 350/96.25; 350/96.28; 264/1.5
[58] Field of Search ............ 350/96.24, 96.25, 96.26, 350/96.28, 96.29, 96.30, 96.33, 96.34; 264/1.5

[56] References Cited

U.S. PATENT DOCUMENTS

| 3,261,349 | 7/1966 | Wallace | 350/96.26 X |
| 3,472,921 | 10/1969 | Fyfe | 264/1.5 |
| 4,000,416 | 12/1976 | Goell | 350/96.33 |
| 4,173,392 | 11/1979 | Ekinaka et al. | 350/96.26 |
| 4,302,073 | 11/1981 | Bendayan et al. | 350/96.3 X |

FOREIGN PATENT DOCUMENTS 56-162704 12/1981 Japan ................... 350/96.34

OTHER PUBLICATIONS

Designing with Crofon Light Guides, E. I. du Pont de Nemours & Company, (Inc.), Wilmington, Delaware, 4-23-69, pp. 1-10.
S. Oikawa, "Plastic Optical Fibre with Improved Transmittance," Electronics Letters, vol. 15, No. 25 (Dec. 6, 1979) pp. 829-830.

Primary Examiner—John Lee
Assistant Examiner—Lester Rushin, III
Attorney, Agent, or Firm—Sughrue, Mion, Zinn, Macpeak & Seas

[57] ABSTRACT

A composite optical fiber for use with a sensor includes an imaging optical fiber which receives information-carrying light that is reflected from a target, and a transparent material that includes the imaging optical fiber in its interior and which transmits an illuminating light from a light source to the target. The light-receiving optical fiber is an integral part of the transparent material, and it has an increased cross-sectional area for transmitting the illuminating light with respect to its overall outside diameter. The optical fiber can be produced by the extrusion technique without arranging a multiplicity of light-transmitting fibers and encasing them within a heat-shrinkable tube.

13 Claims, 9 Drawing Figures

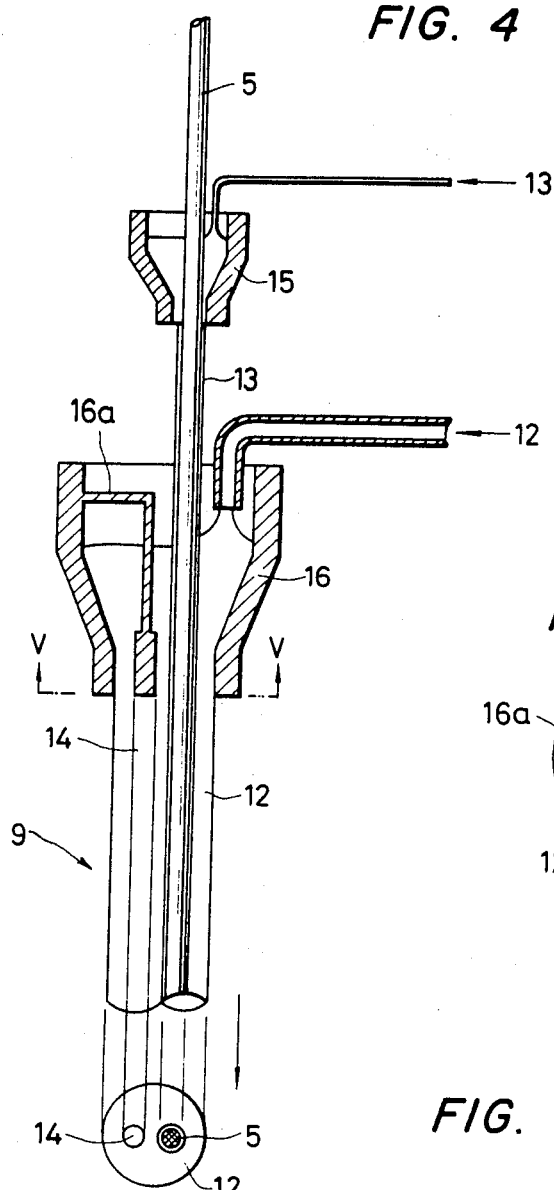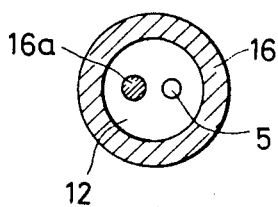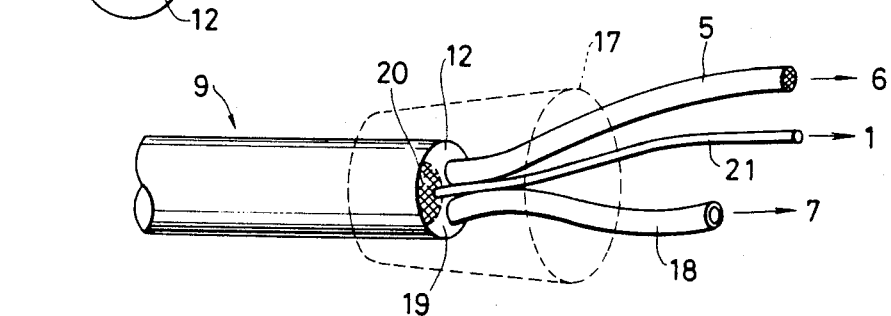

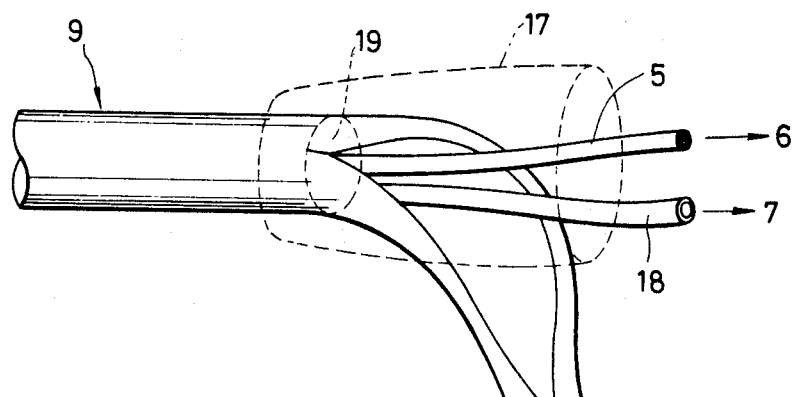
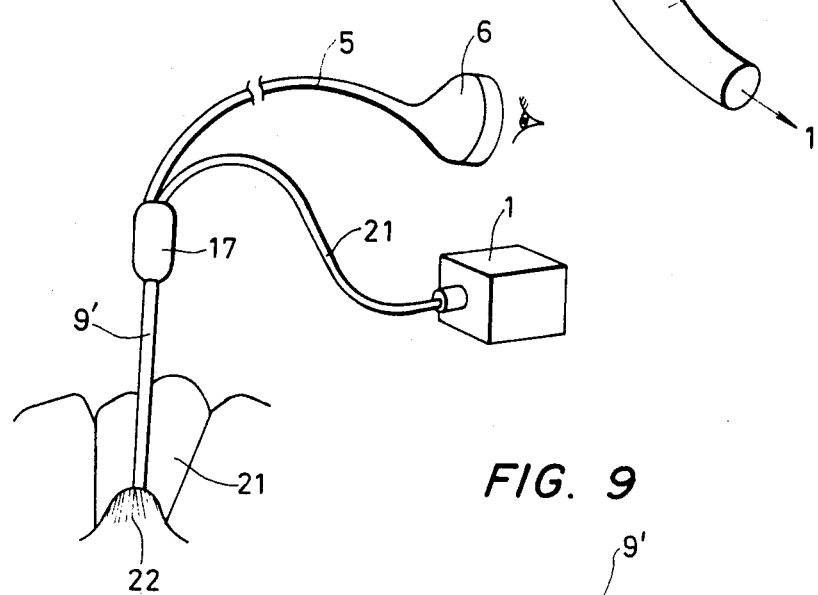
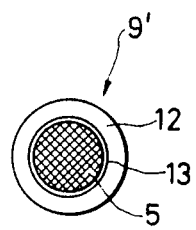

COMPOSITE OPTICAL FIBER AND IMAGING CATHETER AND METHOD FOR PRODUCING THE SAME

BACKGROUND OF THE INVENTION

1. Field of the Invention

The present invention relates to a composite optical fiber, an imaging catheter, and a method for producing the same.

2. Description of the Prior Art

An endoscope (hereinafter referred to as an "imaging catheter") is conventionally used to examine blood vessels, the heart, and the interior of body cavities. A typical imaging catheter is shown in FIG. 1 wherein an illuminating light 4 from a light source 1 is guided through an optical transmission fiber 2 into a blood vessel 3. The image of the target, which is formed by a lens installed at the tip of the catheter, is sent back through an image fiber 5 to a direct-vision adapter 6 which enlarges the image for direct viewing by an operator. If the target is the wall of the blood vessel, and its viewing is obstructed by the blood flowing between the catheter and the target, a physiological saline solution 8 is supplied from a syringe 7 and squirted from the top of the catheter to flush away the blood.

As shown in FIG. 2, a composite optical fiber 9, which makes up the imaging catheter that achieves these functions, comprises the image fiber 5, a brine transferring tube 10 and a plurality of small diameter optical fibers 2' for transmitting the illuminating light, and all of these elements are confined in a casing 11 such as a heat-shrinkable tube. However, since the optical fibers 2' are circular in cross section, a gap exists between them and also between the image fiber 5 and the brine transfer tube 10. As a result, the cross-sectional area, through which the illuminating light is transmitted, is relatively small with respect to the overall cross section of the imaging catheter. Furthermore, the casing or sheath 11 that is used to retain the optical fibers 2' around the image fiber 5 unavoidably adds to the outside diameter of the optical fiber 9. As a further disadvantage, assembling and arranging a plurality of optical illumination transfer fibers 2', an image fiber 5 and a brine transfer tube 10 requires considerable time and labor, and, consequently, the cost of producing the composite optical fiber 9 is increased.

SUMMARY OF THE INVENTION

Therefore, a primary object of the present invention is to provide an optical fiber for use with a sensor that is free from the above-described disadvantages of the conventional product. This object is achieved by a composite optical fiber that comprises an imaging optical fiber which receives information-carrying light from the target and a transparent material that includes said imaging optical fiber in its interior and which transmits an illuminating light from a light source, said imaging optical fiber being an integral part of the transparent material. Said transparent material further contains an opening for permitting a physiological saline solution to flow through it.

A further object of the present invention is to provide a method of making such a composite optical fiber by passing an imaging fiber through a first die while extruding a light-absorbing layer from the first die to coat the imaging fiber with the light-absorbing layer; passing the coated imaging fiber through a second die while extruding a transparent plastic material from the second die to coat the imaging fiber further with the transparent plastic material; and forming an opening in the transparent material as said transparent material is extruded from the second die.

A yet further object of the present invention is to provide a method of making an imaging catheter using the novel, composite optical fiber of the present invention by treating a downstream end of the composite optical fiber with an acid to remove only the transparent material and leave the light-receiving optical fiber exposed; mirror-polishing a part of an exposed surface of the transparent material; spreading a film of matching oil on the mirror-polished surface; connecting an auxiliary optical fiber to the oil-coated, mirror-polished surface; and connecting an exposed end of the light-receiving optical fiber to a sensor.

BRIEF DESCRIPTION OF THE DRAWINGS

FIG. 4 is a side, elevational cross section of an apparatus for fabricating the optical fiber of the present invention;

FIG. 5 is a cross section of FIG. 4 as taken along line V—V;

FIG. 6 diagrammatically shows the structure of a branching mount for an imaging catheter using a composite optical fiber of the present invention;

FIG. 7 diagrammatically shows the structure of another branching mount that can be used with the imaging catheter;

FIG. 8 diagrammatically shows a dental imaging fiber using a composite optical fiber of the present invention; and FIG. 9 is a cross section of the composite optical fiber used with the dental imaging fiber of FIG. 8.

DESCRIPTION OF THE PREFERRED EMBODIMENTS

Preferred embodiments of the present invention are described by reference to FIGS. 3-9.

Figure 1:
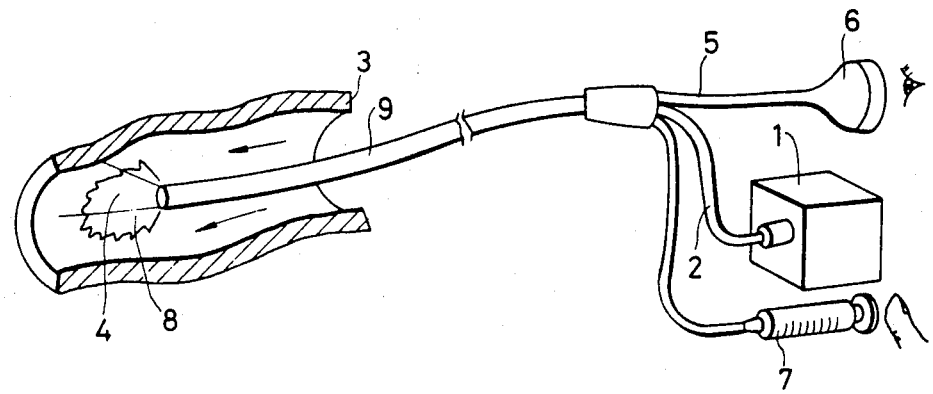
FIG. 1 is a diagrammatic view of a conventional imaging catheter.
Figure 2:
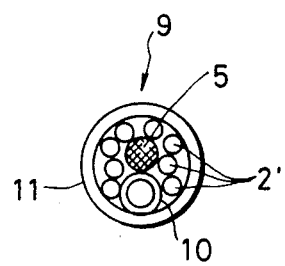
FIG. 2 is a cross section of a composite optical fiber for use with the imaging catheter of FIG. 1.
Figure 3:
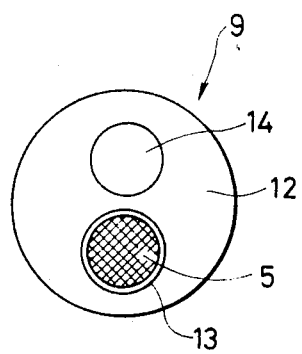
FIG. 3 is a cross section showing a composite optical fiber constructed according to one embodiment of the present invention.

FIG. 3 is a cross section of one embodiment of a composite optical fiber 9 of the present invention. The composite optical fiber 9 comprises an imaging fiber 5 which receives information-carrying light from a target; a transparent material 12 that includes said imaging fiber 5 in its interior and which transmits an illuminating light from a light source to the target; a light-absorbing layer 13 which is formed around the imaging fiber 5; and an opening 14 which is cut through the transparent material 12, parallel to the imaging fiber 5, for permitting the flow of a physiological saline solution.

The imaging fiber 5 is prepared by arranging a plurality of optical fibers in a quartz tube, in a side-by-side assembly, and drawing the assembly to form finer filaments. The light-absorbing layer 13 prevents the leakage of light from the imaging fiber 5 and is made of a material that has a low light transmittance and a higher refractive index than quartz. A suitable example is a hard silicone resin mixed with a fine carbon powder. The transparent material 12 is made of a material which has a high light transmittance such as polymethyl methacrylate, polystyrene or polycarbonate, and it may contain a cladding to eliminate surface flaws, dirt or other factors which may reduce the transmission efficiency of the illuminating light. A suitable cladding may be formed by coating the inner surface of the transparent material 12 and the outer surface of the brine conduit 14 with a plastic which has a lower index of refraction than the transparent material. The cladding on the transparent material 12 may be further coated with a fluorinated resin, such as Teflon ®, to provide better slip and more effective protection from surface flaws and dirt.

The imaging fiber 5 is formed as an integral part of the plastic transparent material 12, and this can be achieved by extrusion using an apparatus of the type illustrated in FIGS. 4 and 5. As the imaging fiber 5 is passed through a die 15, it is coated with a light-absorbing layer 13 which is also extruded from the die 15. Then, the imaging fiber 5, with the light-absorbing layer 13 coated onto it, is passed through a lower die 16 to form a transparent plastic material 12. At the same time, an opening 14, which forms the passage for the physiological saline, is formed in the transparent material 12 by means of an element 16a which is installed in the die 16. The resulting composite optical fiber 9 emerges from the bottom of the die 5 and is continuously wound on a capstan take-up roller (not shown) in the direction indicated by the arrow.

An imaging catheter is prepared from the composite optical fiber 9 by the following method. As shown in FIG. 6, the downstream part of the composite optical fiber, which is to be equipped with a branching mount 17, is treated with sulfuric acid or the like to remove the transparent material 12 and leave only the image fiber 5 behind. A tube 18, which is connected to a syringe (not shown), is inserted into the exposed brine conduit 14 and fixed by a suitable adhesive. Part of the exposed surface 19 of the transparent material 12 is mirror-polished to provide a mirror-smooth surface 20, and one end of an auxiliary optical fiber 21 for transmitting illuminating light is connected to a light source (not shown) and also attached to the mirror-smooth surface 20 with a film of matching oil which is spread on that surface. The illuminating light is then fed to the transparent plastic material 12 after it has been guided through this auxiliary optical fiber 21. The downstream end of the image fiber 5 is connected to a direct-vision adapter (not shown), and the branching section of the optical fiber 9 is covered with the branching mount 17 to protect the joint.

FIG. 7 shows the structure of another branching mount 17 that can be used with the imaging fiber of the present invention. In this embodiment, the part of the optical fiber which is to be equipped with the branching mount 17 and the downstream portion of the optical fiber are split into two portions in the longitudinal direction, and the image fiber 5 is then separated from the transparent material 12. As in the embodiment shown in FIG. 6, a tube 18 is inserted into the exposed brine conduit 14 and fixed by an adhesive. The split portions of the transparent material 12 which extend from the branching mount 17 are joined by heating or another suitable means, and the downstream end of the so-joined transparent material 12 is connected to the light source (not shown).

FIGS. 8 and 9 show an embodiment in which the optical fiber of the present invention is used as a dental imaging fiber for examining the interior of a tooth 21 for the gingiva 22. In practice, a small hole is cut down to the gingiva 22 in the tooth 21, and the tip of the optical fiber 9', including the light-transmitting fiber and light-receiving fiber, is inserted into that hole. The outside diameter of the optical fiber 9', when used as a dental imaging fiber, must not exceed 0.7 mm, and this has been impossible when the conventional fiber arrangement has been used. However, the optical fiber 9' of the present invention satisfies this rigorous dimensional requirement by forming the transparent, light-transmitting plastic material 12 concentric around, and as an integral part of, the imaging fiber 5 with the light-absorbing layer 13, as shown in FIG. 9.

The optical fiber of the present invention can be used as an imaging catheter with an endoscope for examining blood vessels or the heart, and it can also be used as an imaging catheter with an endoscope in dentistry, ophthalmology, otolarynglogy or urology. By replacing the imaging fiber with an ordinary light-receiving optical fiber, the product of the present invention can be used with $SO_2$ sensors, heart rate and output sensors, and medical and industrial spectroscopic analyzers.

As described above, the optical fiber of the present invention does not have a gap formed between the transparent, light-receiving material, the imaging optical fiber, or the brine conduit; therefore, it has an increased cross-sectional area for transmitting the illuminating light with respect to the overall outside diameter of the optical fiber. Moreover, the optical fiber of the present invention can be continuously and efficiently produced by the extrusion technique at low cost, without arranging a multiplicity of light-transmitting fibers and encasing them with a heat-shrinkable tube. As a further advantage, the absence of a gap between the transparent, light-transmitting material and the imaging optical fiber, and the elimination of a heat-shrinkable tube as an outer sheath, provides a fine optical fiber that can be easily assembled into or branched from an imaging fiber system.

We claim:

1. A composite optical fiber, comprising:
   a light-receiving imaging optical fiber, having a first index of refraction, which transmits information-carrying light reflected from a target to a sensor; and
   a first transparent sheath, having a second index of refraction which is lower than said first index of refraction, which transmits illuminating light from a light source to a target to be viewed, said light-receiving imaging optical fiber being contained within an interior portion of said transparent sheath and is an integral part thereof, wherein said transparent material is extruded to cover said light-receiving optical fiber; and
   a light-absorbing layer formed around said imaging optical fiber and within said interior portion of said transparent material for preventing leakage of reflected light from said transparent material to said imaging optical fiber, said light-absorbing layer having an index of refraction lower than said first index of refraction.

2. The composite optical fiber as claimed in claim 1, wherein said light-absorbing layer consists essentially of a hard silicone resin mixed with a fine carbon powder, said light-absorbing layer having a low light transmittance and a refractive index higher than quartz.

3. The composite optical fiber as claimed in claim 1, wherein said transparent material is made of a material having a high light transmittance, said high light transmittance material being selected from the group consisting of polymethyl methacrylate, polystyrene, and polycarbonate.

4. The composite optical fiber as claimed in claim 1, further comprising a liquid passage formed within said transparent material, said liquid passage being substantially parallel with said light-receiving optical fiber.

5. The composite optical fiber as claimed in claim 1, further comprising a cladding material layer formed on an inner surface of said transparent material, said cladding material layer having a lower refractive index than said transparent material.

6. The composite optical fiber as claimed in claim 5, further comprising a protective coating located on said cladding material layer.

7. The composite optical fiber as claimed in claim 6, wherein said protective coating consists essentially of a fluorinated resin.

8. The composite optical fiber as claimed in claim 1, further comprising a protective coating formed on a surface of said transparent material.

9. The composite optical fiber as claimed in claim 8, wherein said protective coating consists essentially of a fluorinated resin.

10. A method of making a composite optical fiber, comprising the steps of:
passing a light-receiving optical fiber, having a first index of refraction, through a first die;
extruding a light-absorbing layer, having a second index of refraction lower than said first index of refraction, from said first die to coat said first light-receiving fiber with said light-absorbing layer;
passing said coated light-receiving fiber through a second die;
extruding a transparent plastic material, having an index of refraction greater than said second index of refraction, from said second die to further coat said light-receiving fiber with said transparent material, and forming an opening in said transparent material as said transparent material is extruded from said second die.

11. A method of making an imaging catheter using a composite optical fiber which comprises a light-receiving optical fiber which is contained in an interior portion of a light-transmitting transparent sheath, said light-receiving optical fiber being integrally formed with said transparent sheath, comprising the steps of:
treating a downstream end of said composite optical fiber with an acid to remove only said transparent sheath and leave said light-receiving optical fiber exposed;
mirror-polishing a part of an exposed surface of said transparent sheath;
spreading a film of matching oil on said mirror-polished surface;
connecting an auxiliary optical fiber to said oil coated, mirror-polished surface; and
connecting an exposed end of said light-receiving optical fiber to a sensor.

12. The method as claimed in claim 11, wherein said transparent sheath has an exposed brine conduit, said method further comprising the steps of inserting a tube into said exposed brine conduit of said transparent material; and
fixing said tube to said exposed brine conduit with an adhesive.

13. A method of making an imaging catheter using a composite optical fiber which comprises a light-receiving optical fiber which is contained in an interior portion of a light-transmitting transparent sheath, said light-receiving optical fiber being integrally formed with said light-transmitting transparent sheath, comprising the steps of:
splitting a downstream portion of said transparent sheath, into two portions along a longitudinal direction of said composite optical fiber;
separating said light-receiving optical fiber from said two portions of said transparent sheath;
joining said two portions of said transparent sheath;
connecting said joined portions of said transparent sheath to a light source; and
connecting said separated light-receiving optical fiber to a sensor.

* * * * *